United States Patent
Happ et al.

(10) Patent No.: US 7,388,667 B2
(45) Date of Patent: Jun. 17, 2008

(54) OPTICAL DETERMINATION OF RESISTIVITY OF PHASE CHANGE MATERIALS

(75) Inventors: Thomas Happ, Tarrytown, NY (US); Shoaib Hasan Zaidi, Poughkeepsie, NY (US)

(73) Assignee: Infineon Technologies AG, Munich (DE)

( * ) Notice: Subject to any disclaimer, the term of this patent is extended or adjusted under 35 U.S.C. 154(b) by 160 days.

(21) Appl. No.: 11/240,026

(22) Filed: Sep. 30, 2005

(65) Prior Publication Data
US 2007/0076191 A1  Apr. 5, 2007

(51) Int. Cl.
G01N 21/55 (2006.01)
(52) U.S. Cl. ...................................... 356/445
(58) Field of Classification Search ...................... None
See application file for complete search history.

(56) References Cited

U.S. PATENT DOCUMENTS

| | | | | |
|---|---|---|---|---|
| 4,508,931 A | * | 4/1985 | Michel et al. | 136/255 |
| 5,563,508 A | | 10/1996 | Tatah | |
| 5,596,522 A | * | 1/1997 | Ovshinsky et al. | 365/113 |
| 5,706,212 A | * | 1/1998 | Thompson et al. | 702/85 |
| 6,128,084 A | * | 10/2000 | Nanbu et al. | 356/369 |
| 6,573,737 B1 | | 6/2003 | Lyon et al. | |
| 6,906,801 B2 | | 6/2005 | Borden et al. | |

2002/0186381 A1 * 12/2002 Subrahmanyan et al. ... 356/630

FOREIGN PATENT DOCUMENTS

EP  827192 A2 *  3/1998

OTHER PUBLICATIONS

H. Horii et al., "A novel cell technology using N-doped GeSbTe films for phase change RAM", VLSI, 2003.
Y. N. Hwang et al., "Full integration and reliability evaluation of phase-change RAM based in 0.24μm-CMOS technologies", VLSI, 2003.
S. Lai et al., "OUM-a 180 nm nonvolatile memory cell element technology for stand alone and embedded applications", IEDM, 2001.
T. Lowrey et al., "Characteristics of OUM phase change materials and devices for high density non-volatile commodity and emvedded applications", MRS Symposium Proceedings vol. 803, Symposium HH, p. 101, 2003.
Y.H. Ha et al., "An edge contact type cell for phase change RAM featuring very low power consumption", VLSI, 2003.
S.L. Cho et al., "A Novel Cell Technology for Phase Change RAM", available at http://www.epcos.org/pdf_2004/17paper_cho.pdf.

* cited by examiner

*Primary Examiner*—Tarifur Chowdhury
*Assistant Examiner*—Jonathon D Cook
(74) *Attorney, Agent, or Firm*—Dicke, Billig & Czaja, PLLC

(57) ABSTRACT

A system includes a non-contacting optical measurement instrument and a controller. The non-contacting optical measurement instrument is configured to obtain a measurement of a phase-change material. The controller is configured to determine a resistivity of the phase-change material based on the measurement.

30 Claims, 6 Drawing Sheets

OPTICAL DETERMINATION OF RESISTIVITY OF PHASE CHANGE MATERIALS

BACKGROUND

Phase-change materials exhibit at least two different states. The states of phase-change material may be referenced to as amorphous and crystalline states. The states may be distinguished because the amorphous state generally exhibits higher resistivity than does the crystalline state. Generally, the amorphous state involves a more disordered atomic structure, while the crystalline state is an ordered lattice.

Phase change in the phase-change materials may be induced reversibly. In this way, the phase-change material may change from the amorphous state to the crystalline state, and from the crystalline state to the amorphous state, in response to temperature changes. The temperature changes to the phase-change material may be achieved in a variety of ways. For example, a laser can be directed to the phase-change material, current may be driven through the phase-change material, or current can be fed through a resistive heater adjacent the phase-change material. With any of these methods, controllable heating of the phase-change material causes controllable phase change within the phase-change material.

The heating current needed to reach a fixed temperature such as the crystallization or melting temperature of the phase-change material varies considerably with the resistivity of the phase-change material. Typically, the electronic circuitry for providing the heating current is designed to work with a specified range of resistivities. Consequently, determination and control of resistivity is essential for successful device performance.

Typically, resistivity is determined by using a four point probe. The four point probe physically contacts the material to be tested. For production wafers, physical contact may contaminate the product wafer and/or damage the surface of the product wafer. Therefore, wasteful monitor wafers are typically used in place of product wafers if four point probe measurements are to be performed to measure resistivity. In addition, the probes typically have a spacing of approximately one millimeter. Therefore, several millimeter sized areas are dedicated for measurements on the wafer surface when using a four point probe. Four point probe measurements are also often performed at the edge of the wafer.

SUMMARY

One embodiment of the present invention provides a system. The system includes a non-contacting optical measurement instrument and a controller. The non-contacting optical measurement instrument is configured to obtain a measurement of a phase-change material. The controller is configured to determine a resistivity of the phase-change material based on the measurement.

BRIEF DESCRIPTION OF THE DRAWINGS

Embodiments of the invention are better understood with reference to the following drawings. The elements of the drawings are not necessarily to scale relative to each other. Like reference numerals designate corresponding similar parts.

DETAILED DESCRIPTION

Figure 1:
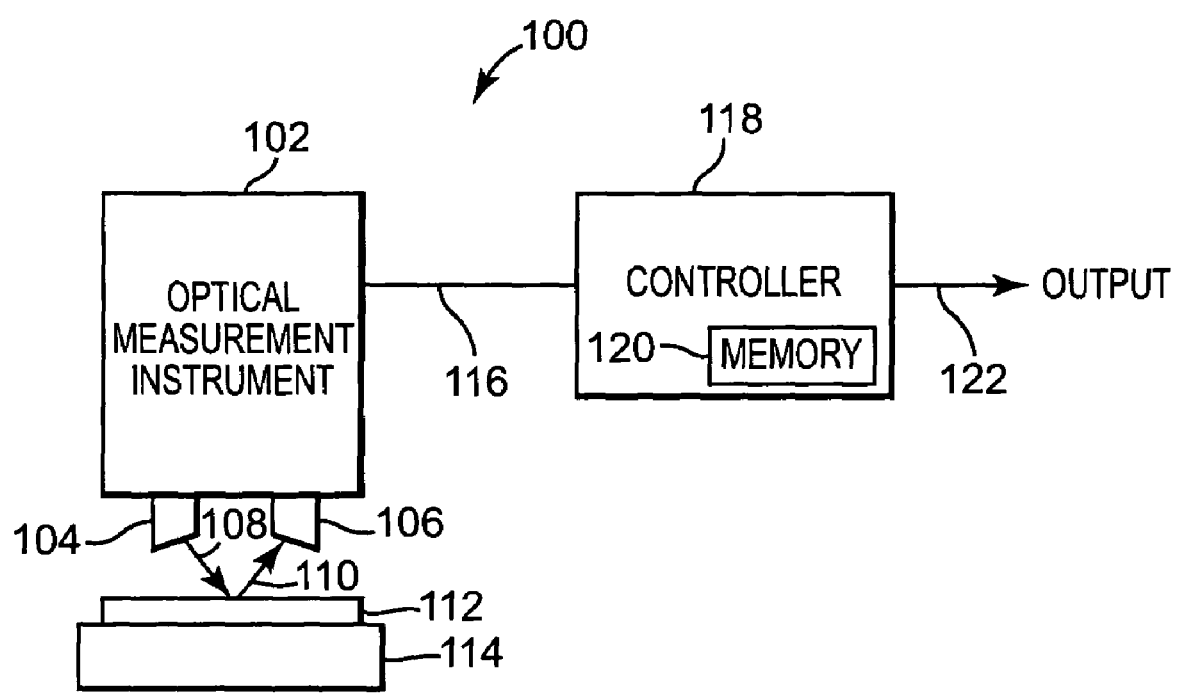
FIG. 1 is a block diagram illustrating one embodiment of an optical measurement system for determining the resistivity of a sample.

FIG. 1 is a block diagram illustrating one embodiment of an optical measurement system 100 for determining the resistivity of a sample 112. Optical measurement system 100 provides a non-contact method for determining the resistivity of phase-change materials. The resistivity of a phase-change material such as GST varies based on its composition and the amount of doping. Typical dopant materials used include nitrogen, oxygen, or silicon. The resistivity of a sample of doped GST or another suitable phase-change material can be determined by comparing the optical characteristics of the sample with a sample having a known resistivity. In one embodiment, the optical characteristic used to determine the resistivity is the refractive index. The refractive index of the phase-change material is determined using optical techniques, such as reflectometry or ellipsometry. The refractive index is then correlated to the resistivity by using empirically generated correlation data.

This optical method for determining resistivity provides several advantages over the four point probe method. The optical method will not contaminate or damage the surface of a wafer. In addition, typical reflectometers have approximately 50 µm spot sizes and laser based ellipsometers can have spot sizes of 5 by 10 µm. The combination of non-contact and small test areas for measurement allows the technique to be used on production wafers. In addition, the entire wafer surface can be profiled to determine processing uniformities.

Optical measurement system 100 includes an optical measurement instrument 102, a stage 114, and a controller 118. Optical measurement instrument 102 includes a light source 104 and a detector 106. A sample, such as a product wafer 112 including a phase-change material film, is positioned on stage 114 for analysis by optical measurement instrument 102. Optical measurement instrument 102 is electrically coupled to controller 118 through communication link 116. Controller 118 includes a memory 120 for storing resistivity data. Controller 118 provides the OUTPUT signal on OUTPUT signal path 122.

Sample 112 includes a doped phase-change material film. The phase-change material may be made up of a variety of materials in accordance with the present invention. Generally, chalcogenide alloys that contain one or more elements from group VI of the periodic table are useful as such materials. In one embodiment, the phase-change material is made up of a chalcogenide compound material, such as GeSbTe (GST), SbTe, or AgInSbTe. In another embodiment, the phase-change material can be chalcogen free, such as GeSb, GaSb, or GeGaSb. The dopant can be made up from a variety of materials. In one embodiment, the dopant comprises nitrogen. In another embodiment, the dopant comprises oxygen, silicon, aluminum, phosphorous, other suitable dopant materials, or combinations thereof.

Optical measurement instrument 102 is an ellipsometer, reflectometer, or other suitable optical measurement instrument. An ellipsometer uses polarized light to characterize thin films, surfaces, and material microstructures. An ellipsometer determines the relative phase change in a beam of reflected polarized light. A reflectometer measures reflectivity, which is the ratio of the intensity of a wave after reflection to the intensity of the wave before reflection. Light source 104 includes a laser light source or broadband light source and optics to direct light onto the surface of sample 112. Detector 106 includes a photodetector and optics to detect light reflected from the surface of sample 112. In one embodiment, optical measurement instrument 102 provides data, such as Psi and Delta (for an ellipsometer), reflectivity (for a reflectometer), or other suitable data from which the complex refractive index of sample 112 can be determined, to controller 118 through communication link 116. In another embodiment, optical measurement instrument 102 determines the refractive index based on measurement data of sample 112 and provides the refractive index to controller 118.

Controller 118 receives the optical measurement data from optical measurement instrument 102 and determines the refractive index or receives the refractive index from optical measurement instrument 102. Memory 120 stores data correlating the refractive index to the resistivity of the phase-change material. In one embodiment, the correlation data is stored in a database. Controller 118 determines the resistivity of the phase-change material of sample 112 based on the refractive index using the data stored in memory 120. In one embodiment, controller 118 outputs the resistivity data on OUTPUT signal path 122.

In operation, a sample 112 including a doped phase-change material film, such as a nitrogen doped GST film, is placed on stage 114 for analysis. Optical measurement instrument 102 directs light from light source 104 onto the surface of sample 112 as indicated at 108. Light is reflected from sample 112 as indicated at 110. Detector 106 of optical measurement instrument 102 detects the light indicated at 110 reflected from sample 112. Based on the detected reflected light, optical measurement instrument 102 provides data for determining the refractive index of sample 112 or determines and provides the refractive index of sample 112. The data for determining the refractive index or the refractive index is passed to controller 118. Controller 118 determines the refractive index or receives the refractive index and determines the resistivity of the phase-change material of sample 112 based on the refractive index. In one embodiment, controller 118 outputs the resistivity of the phase-change material of sample 112 on OUTOUT signal path 122.

Figure 2A:
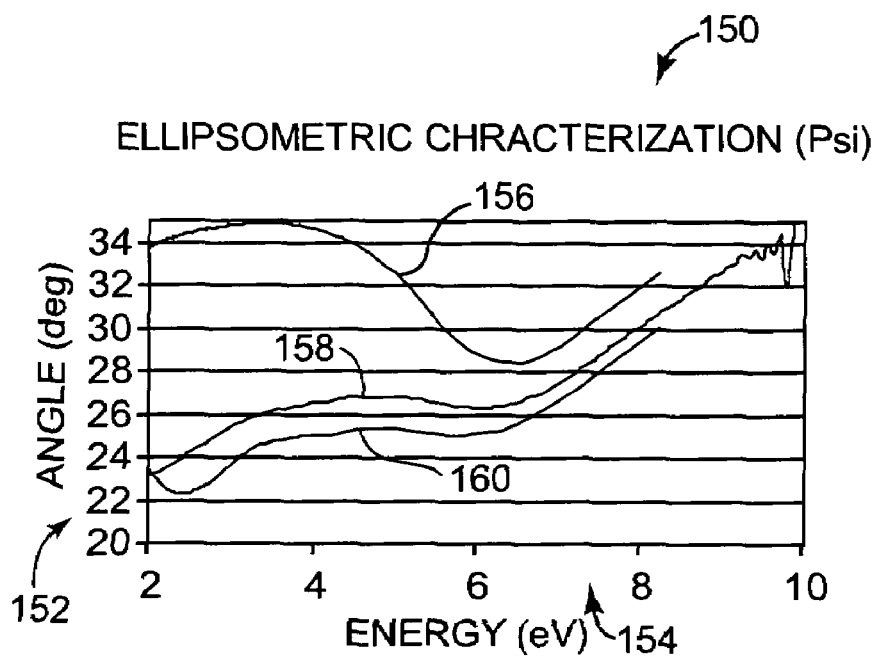
FIG. 2A is a graph illustrating one embodiment of an ellipsometric characterization of Psi for three different doping levels of GST films.

FIG. 2A is a graph 150 illustrating one embodiment of an ellipsometric characterization of Psi for three different doping levels of GST films. Ellipsometry can be used to observe variations in the film properties due to the different doping levels. Graph 150 illustrates Psi for three wafer samples 112 having 80 nm GST films doped with nitrogen ($N_2$). Graph 150 includes angle 152 in degrees on the y-axis and light energy in electron volts (eV) 154 on the x-axis. Line 156 illustrates the characterization of Psi for a GST film with no $N_2$ doping. Line 158 illustrates the characterization of Psi for a GST film doped with 1 sccm $N_2$. Line 160 illustrates the characterization of Psi for a GST film doped with 1.74 sccm $N_2$. As illustrated by graph 150, different doping levels affect the ellipsometric characterization of Psi for phase-change materials.

Figure 2B:
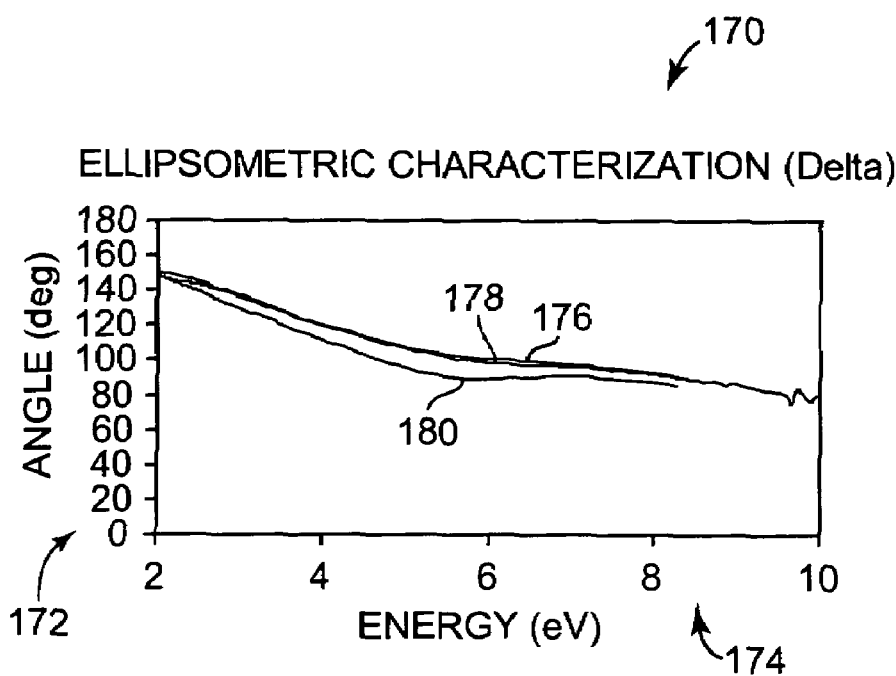
FIG. 2B is a graph illustrating one embodiment of an ellipsometric characterization of Delta for three different doping levels of GST films.

FIG. 2B is a graph 170 illustrating one embodiment of an ellipsometric characterization of Delta for three different doping levels of GST films. Ellipsometry can be used to observe variations in the film properties due to the different doping levels. Graph 170 illustrates three wafer samples 112 having 80 nm GST films doped with nitrogen. Graph 170 includes angle 172 in degrees on the y-axis and light energy in electron volts (eV) 174 on the x-axis. Line 180 illustrates the characterization of Delta for a GST film with no $N_2$ doping. Line 178 illustrates the characterization of Delta for a GST film doped with 1 sccm $N_2$. Line 176 illustrates the characterization of Delta for a GST film doped with 1.74 sccm $N_2$. As illustrated by graph 170, different doping levels affect the ellipsometric characterization of Delta for phase-change materials.

Psi and Delta describe the polarization change between light indicated at 108 provided by light source 104 and light indicated at 110 detected by detector 106 (FIG. 1). In one embodiment, optical measurement instrument 102 determines Psi and Delta for the phase-change material of sample 112. In one embodiment, optical measurement instrument 102 passes Psi and Delta for the phase-change material of sample 112 to controller 118 and controller 118 determines the refractive index for the phase-change material of sample 112 by using the Fresnel Reflection Coefficients. In another embodiment, optical measurement instrument 102 determines the refractive index for the phase-change material of sample 112 based on Psi and Delta for the phase-change material of sample 112 and by using the Fresnel Reflection Coefficients and passes the refractive index of the phase-change material of sample 112 to controller 118.

Figure 3:
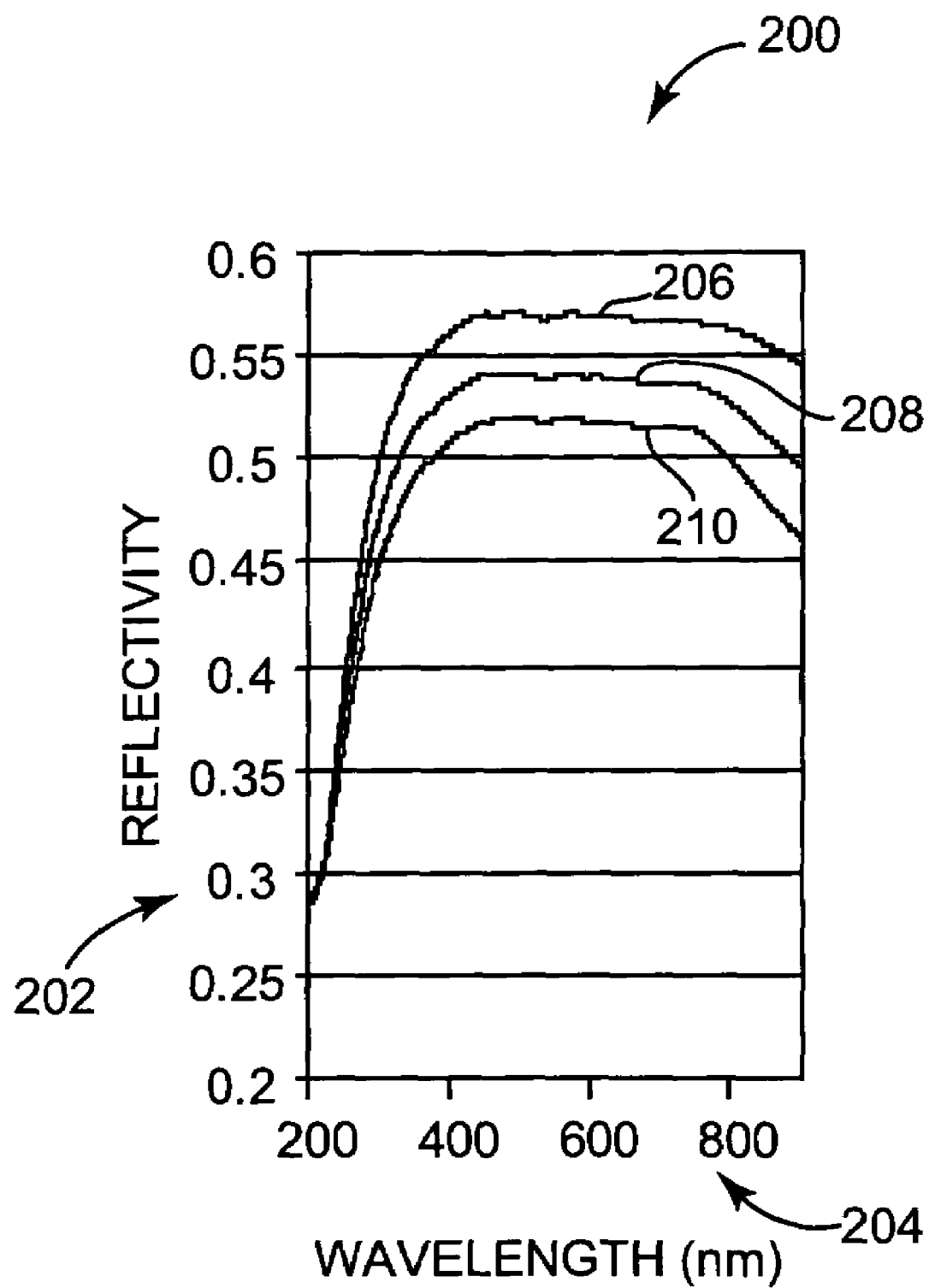
FIG. 3 is a graph illustrating one embodiment of reflectivity versus wavelength for three different doping levels of GST films.

FIG. 3 is a graph 200 illustrating one embodiment of reflectivity 202 versus wavelength 204 in nanometers (nm) for three different doping levels of GST films. Reflectometry can be used to observe variations in the film properties due to the different doping levels. Line 206 illustrates reflectivity 202 versus wavelength 204 for a GST film doped with 3 sccm $N_2$. Line 208 illustrates reflectivity 202 versus wavelength 204 for a GST film doped with 5 sccm $N_2$. Line 210 illustrates reflectivity 202 versus wavelength 204 for a GST film doped with 7 sccm $N_2$. As illustrated by graph 200, different doping levels affect the reflectivity of phase-change materials.

In one embodiment, optical measurement instrument 102 determines the reflectivity of the phase-change material of sample 112. In one embodiment, optical measurement instrument 112 passes the reflectivity of the phase-change material of sample 112 to controller 118 and controller 118 determines the refractive index for the phase-change material of sample 112 based on the reflectivity. In another embodiment, optical measurement instrument 102 determines the refractive index for the phase-change material of sample 112 based on the reflectivity of the phase-change material of sample 112 and passes the refractive index of the phase-change material of sample 112 to controller 118.

Figure 4:
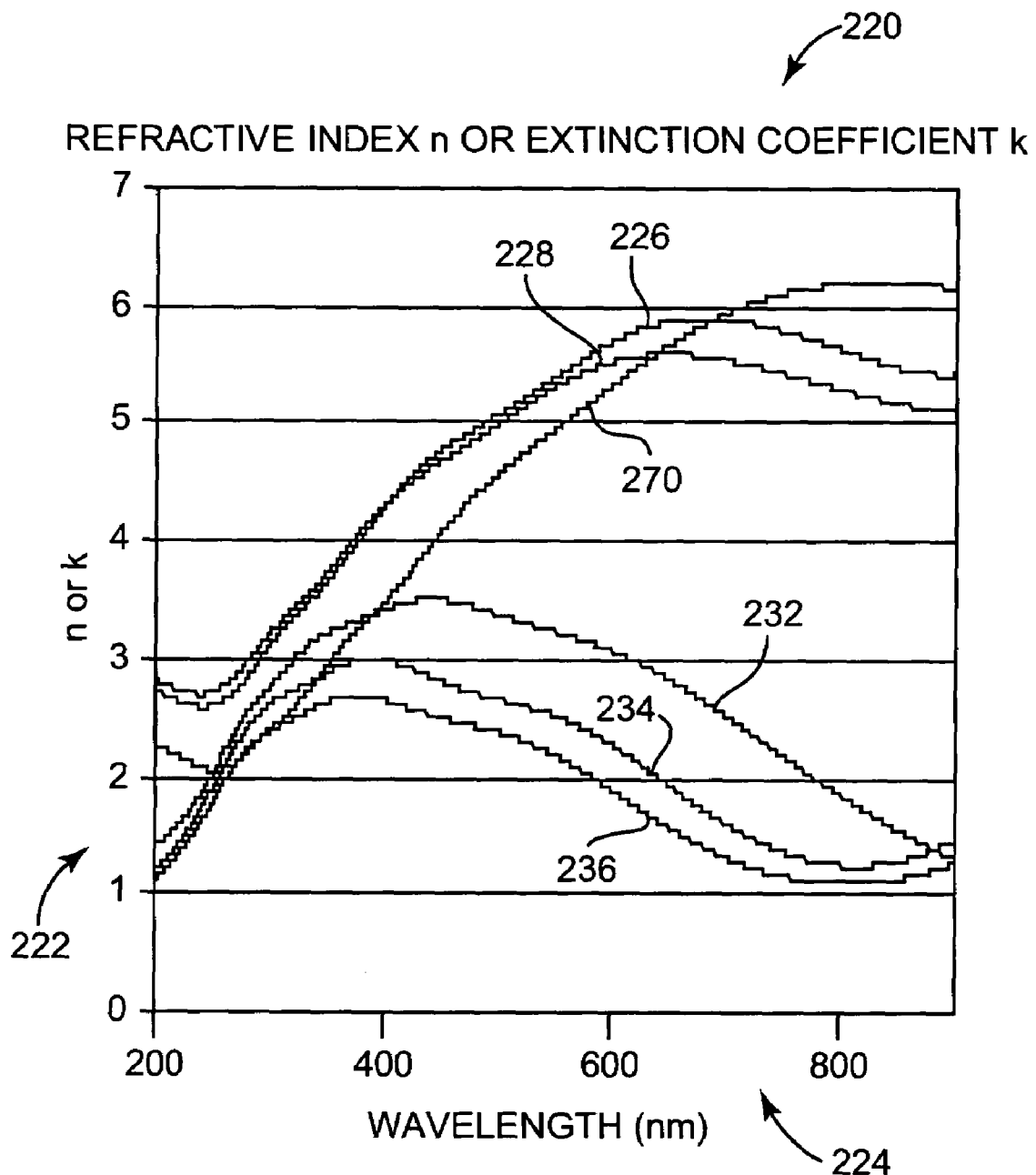
FIG. 4 is a graph illustrating one embodiment of refractive index (real and imaginary parts, n and k) versus wavelength for three different doping levels of GST films.

FIG. 4 is a graph 220 illustrating one embodiment of refractive index 222 (real and imaginary parts, n and k) versus wavelength 224 in nanometers (nm) for three different doping levels of GST films. The refractive index can be used to indicate variations in the film properties due to the different film resistivities caused by the different doping levels. Line 230 illustrates n 222 versus wavelength 224 for a GST film doped with 3 sccm $N_2$. Line 226 illustrates n 222 versus wavelength 224 for a GST film doped with 5 sccm N$_2$. Line 228 illustrates n 222 versus wavelength 224 for a GST film doped with 8 sccm N$_2$. Line 232 illustrates k 222 versus wavelength 224 for a GST film doped with 3 sccm N$_2$. Line 234 illustrates k 222 versus wavelength 224 for a GST film doped with 5 sccm N$_2$. Line 236 illustrates k 222 versus wavelength 224 for a GST film doped with 8 sccm N$_2$. As illustrated by graph 220, different doping levels affect the refractive index of phase-change materials.

In one embodiment, optical measurement instrument 102 determines the refractive index for the phase-change material of sample 112 and passes the refractive index of the phase-change material of sample 112 to controller 118. In another embodiment, controller 118 determines the refractive index of the phase-change material of sample 112 based on data received from optical measurement instrument 102.

Figure 5A:
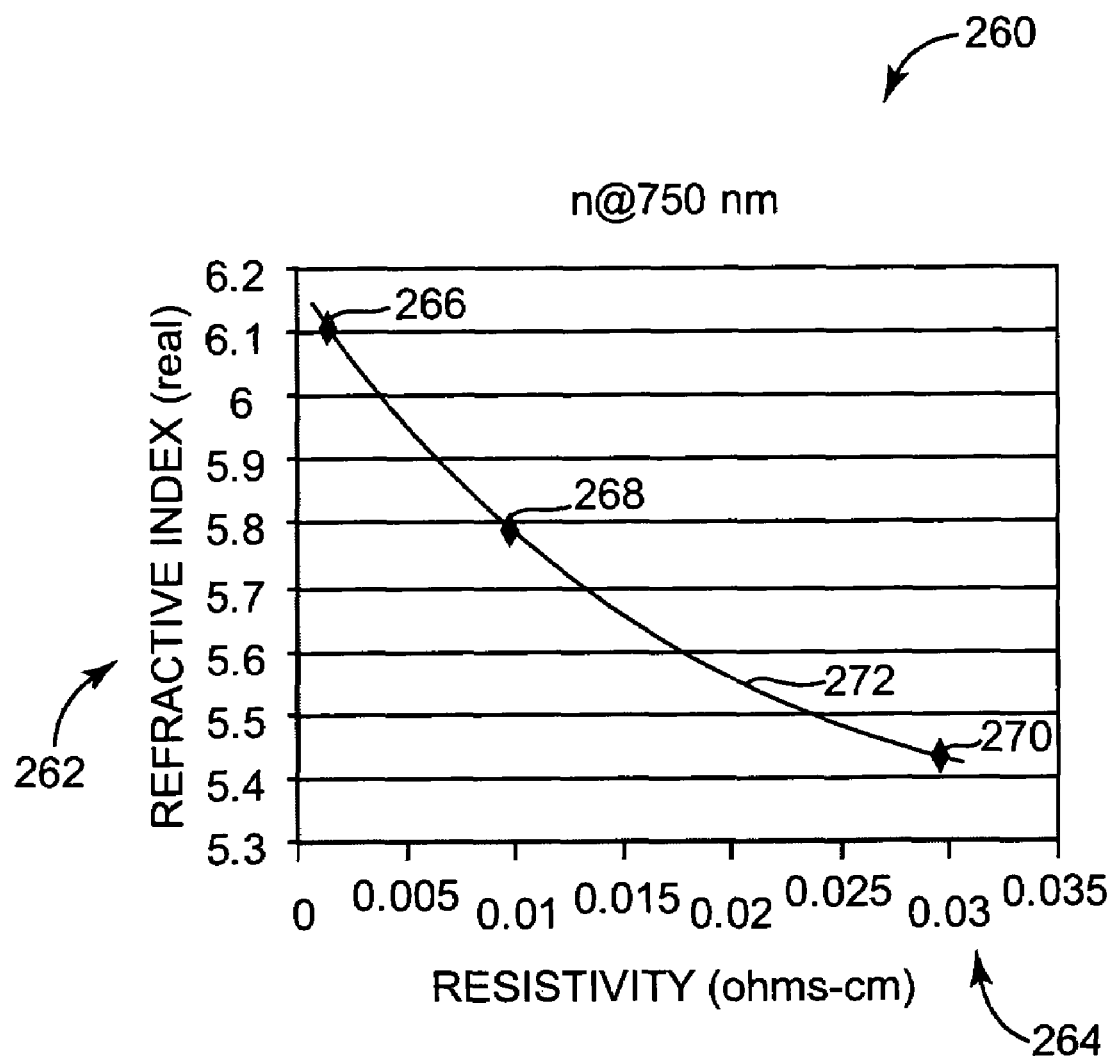
FIG. 5A is a graph illustrating one embodiment of refractive index (real part, n) versus resistivity for three different doping levels of GST films.

FIG. 5A is a graph 260 illustrating one embodiment of refractive index 262 (real part, n) versus resistivity 264 in ohm centimeters. In this embodiment, n is determined at a wavelength of 750 nm. The resistivity 264 for a GST film doped with 3 sccm N$_2$ based on the refractive index 262 is indicated at 266. The resistivity 264 for a GST film doped with 5 sccm N$_2$ based on the refractive index 262 is indicated at 268. The resistivity 264 for a GST film doped with 7 sccm N$_2$ based on the refractive index 262 is indicated at 270. A smooth calibration curve 272 connects data points 266, 268, and 270. Controller 118 correlates the refractive index 262 to the resistivity 264 stored in memory 120 to provide the resistivity for the phase-change material of sample 112 on OUTPUT signal path 122.

Figure 5B:
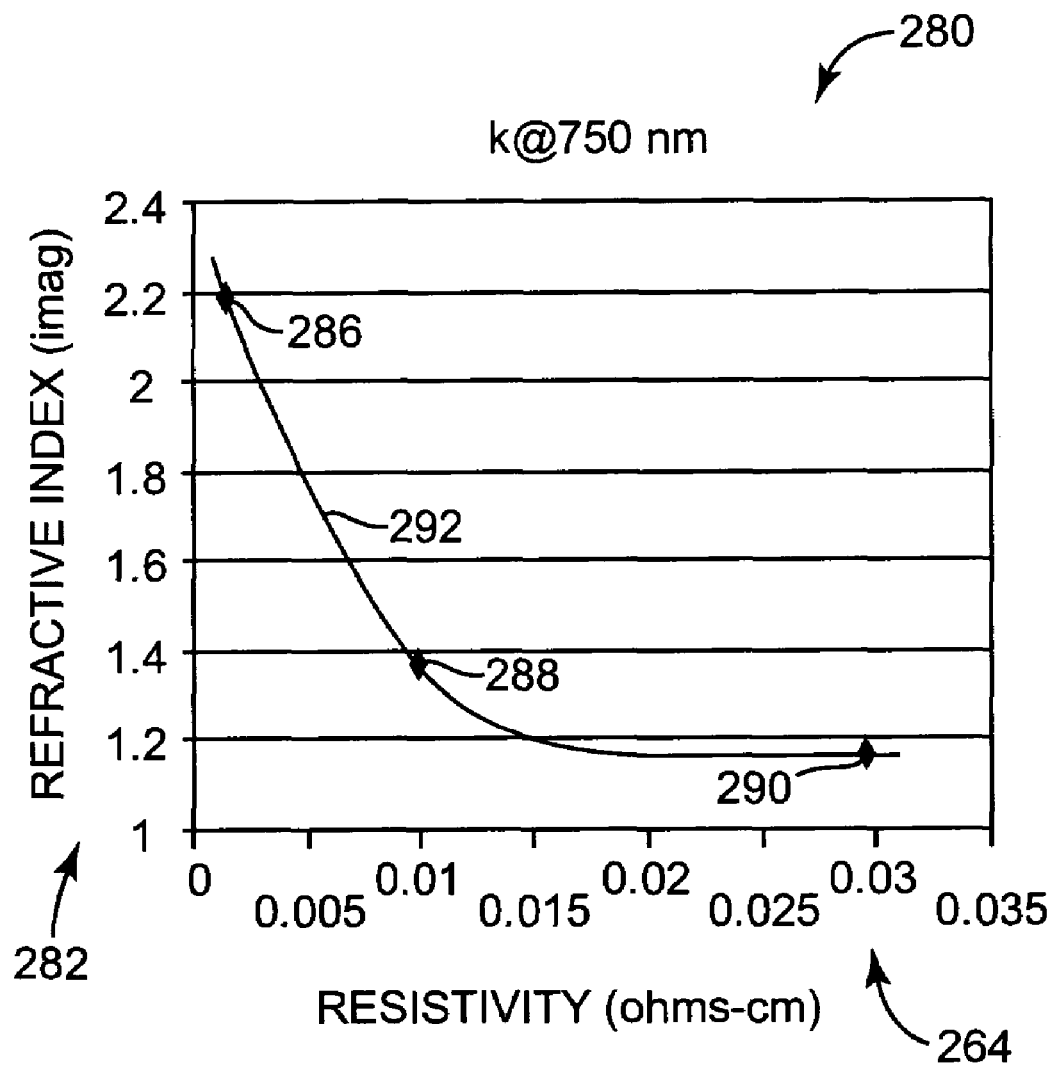
FIG. 5B is a graph illustrating one embodiment of refractive index (imaginary part, k) versus resistivity for three different doping levels of GST films.

FIG. 5B is a graph 280 illustrating one embodiment of refractive index 282 (imaginary part, k) versus resistivity 264 in ohm centimeters. In this embodiment, k is determined at a wavelength of 750 nm. The resistivity 264 for a GST film doped with 3 sccm N$_2$ based on the refractive index 282 is indicated at 286. The resistivity 264 for a GST film doped with 5 sccm N$_2$ based on the refractive index 282 is indicated at 288. The resistivity 264 for a GST film doped with 7 sccm N$_2$ based on the refractive index 282 is indicated at 290. A smooth calibration curve 292 connects data points 286, 288, and 290. Controller 118 correlates the refractive index 282 to the resistivity 264 stored in memory 120 to provide the resistivity for the phase-change material of sample 112 on OUTPUT signal path 122.

Embodiments of the invention provide a non-contact system and method for determining the resistivity of doped phase-change material films based on optical properties of the phase-change material films. Using optical measurement instruments commonly found in semiconductor fabrication facilities, such as ellipsometers or reflectometers, the resistivity of doped phase-change materials on product wafers can be determined quickly in line, in situ during doping, or off line.

What is claimed is:

1. A system comprising:
   a non-contacting optical measurement instrument for obtaining a measurement of a phase-change material; and
   a controller that determines a resistivity of the phase-change material based on the measurement,
   wherein the phase-change material changes between an amorphous state and a crystalline state in response to temperature changes.

2. The system of claim 1, wherein the measurement comprises a refractive index measurement.

3. The system of claim 1, wherein the phase-change material is doped with nitrogen.

4. The system of claim 1, wherein the phase-change material is doped with a material selected from a group consisting of oxygen, silicon, aluminum, and phosphorous.

5. The system of claim 1, wherein the phase-change material comprises a chalcogen free material.

6. The system of claim 1, wherein the phase-change material comprises a chalcogenide.

7. The system of claim 6, wherein the chalcogenide is GeSbTe.

8. A system comprising:
   a non-contacting optical measurement instrument for determining a refractive index of a doped phase-change material on a semiconductor wafer for fabricating phase-change memory devices; and
   a controller that determines a resistivity of the doped phase-change material based on the refractive index,
   wherein the doped phase-change material changes between an amorphous state and a crystalline state in response to temperature changes.

9. The system of claim 8, wherein the non-contacting optical measurement instrument comprises a reflectometer.

10. The system of claim 8, wherein the non-contacting optical measurement instrument comprises an ellipsometer.

11. The system of claim 8, further comprising:
    a database for correlating the refractive index to the resistivity.

12. The system of claim 8, wherein the phase-change material comprises a chalcogenide.

13. The system of claim 8, wherein the phase-change material comprises a chalcogen free material.

14. The system of claim 8, wherein the doped phase-change material comprises a dopant selected from a group consisting of nitrogen, oxygen, silicon, aluminum, and phosphorous.

15. A system for determining resistivity comprising:
    means for determining a refractive index of a phase-change material; and
    means for determining a resistivity of the phase-change material based on the refractive index,
    wherein the phase-change material changes between an amorphous state and a crystalline state in response to temperature changes.

16. The system of claim 15, wherein the means for determining the refractive index comprises means for determining the refractive index of a phase-change material product sample.

17. The system of claim 15, wherein the means for determining the refractive index comprises means for determining the refractive index of a doped chalcogenide phase-change material.

18. The system of claim 17, wherein the means for determining the refractive index of the doped chalcogenide phase-change material comprises means for determining the refractive index of a nitrogen doped chalcogenide phase-change material.

19. The system of claim 17, wherein the means for determining the refractive index of the doped chalcogenide phase-change material comprises means for determining the refractive index of nitrogen doped GeSbTe.

20. A method for determining resistivity, the method comprising:
    obtaining an optical measurement of a phase-change material that chances between an amorphous state and a crystalline state in response to temperature changes; and
    determining a resistivity of the phase-change material based on the optical measurement.

21. The method of claim 20, wherein obtaining the optical measurement of the phase-change material comprises obtaining the optical measurement of a phase-change material doped with nitrogen.

22. The method of claim 20, wherein obtaining the optical measurement comprises obtaining a reflectometer measurement.

23. The method of claim 20, wherein obtaining the optical measurement comprises obtaining an ellipsometer measurement.

24. The method of claim 20, wherein obtaining the optical measurement of the phase-change material comprises obtaining the optical measurement of a phase-change material comprising a chalcogenide.

25. A method for determining resistivity, the method comprising:

determining a refractive index of a doped phase-change material that changes between an amorphous state and a crystalline state in response to temperature changes; and determining a resistivity of the phase-change material based on the refractive index.

26. The method of claim 25, wherein determining the refractive index comprises determining the refractive index using reflectometry.

27. The method of claim 25, wherein determining the refractive index comprises determining the refractive index using ellipsometry.

28. The method of claim 25, wherein determining the resistivity comprises correlating the refractive index to a corresponding previously stored resistivity value.

29. The method of claim 25, wherein determining the refractive index comprises determining the refractive index of a phase-change material product sample.

30. The method of claim 29, further comprising:

determining a resistivity profile for the phase-change material product sample.

* * * * *